(12) United States Patent
Liu et al.

(10) Patent No.: US 8,569,452 B2
(45) Date of Patent: Oct. 29, 2013

(54) PREPARATION OF PHALLOIDIN AND ITS DERIVATIVES

(75) Inventors: Baosheng Liu, Cupertino, CA (US); Jianheng Zhang, San Jose, CA (US)

(73) Assignee: American Peptide Company, Inc., Sunnyvale, CA (US)

( * ) Notice: Subject to any disclaimer, the term of this patent is extended or adjusted under 35 U.S.C. 154(b) by 82 days.

(21) Appl. No.: 13/385,265

(22) Filed: Feb. 10, 2012

(65) Prior Publication Data

US 2012/0214968 A1    Aug. 23, 2012

Related U.S. Application Data

(60) Provisional application No. 61/463,422, filed on Feb. 17, 2011.

(51) Int. Cl.
*A61K 38/12* (2006.01)

(52) U.S. Cl.
CPC .................................... *A61K 38/12* (2013.01)
USPC ........................................................ 530/334

(58) Field of Classification Search
None
See application file for complete search history.

(56) References Cited

U.S. PATENT DOCUMENTS 7,964,702 B2    6/2011   Lokey

OTHER PUBLICATIONS

Weiland, T., et al., "Einige vom Ketophalloidin abgeleitete, in der biochemischen Forschung anwendbar Dithiolane," Liebigs Ann. Chem. (1980) pp. 416-424.
Weiland, T., et al., "Analogs of phalloidin," Int. J. Pept. Protein Res. (1983) 21, pp. 3-10.
Schuresko, L. and Lokey, R., "A Practical Solid-Phase Synthesis of Glu7-Phalloidin and Entry into Fluorescent F-Actin-..," Angew. Chem. Int. Ed. (2007) 46, pp. 3547-3549.
Fahrenholz, F., "Synthese des Norphalloins und eines Monocyclus mit 18 gliedrigem Ring," Liebigs Ann. Chem. (1971) 743, pp. 83-94.
Munekata, E., et al., "Totalsynthese von Phalloin und [Leu7]-phalloin," Liebigs Ann. Chem. (1977) pp. 1758-1765.
Weiland, T., et al., "Optimierung der Synthese von Indolyl-(2)-thioathem aus Derivaten des Tryptophans und des Cysteins," Leibigs Ann. Chem. (1969) 727, pp. 138-142.
Savige, W. and Fontana, A., "A Novel Synthesis of 2-thioether Derivatives of Tryptophan," Int. J. Pept. Protein Res (1980) 15, pp. 102-112.
Savige, W. and Fontana, A., "New Method of Linking Tryptophan to Cysteine Sulphydryl Groups in Peptides and Proteins," J. Chem. Soc., Chem. Comm. (1976) pp. 600-601.
Savige, W., "New Oxidation Products of Tryptophan," Aust. J. Chem. (1975) 28, pp. 2275-2278.
Zanotti, G., et al., "Solid State and Solution Conformation of [Ala7]-Phalloidin: A Synthetic Phallotixin Analogue," Chem. Eur. J. (2001) 7, No. 7, 1479-1485.
Zanotti, G., et al., "Phalloidin Synthetic Analogues: Structural Requirements in the Interation with F-Actin," Chem. Eur. J. (2001) 7, No. 21, 4665-4673.
Sieber, P., et al., "Iodine Oxidation of S-Trityl- and S-Acetamidomethyl-cysteine-peptides Containing Tryptophan ...," Helv. Chim. Acta. (1980) 63, pp. 2358-2363.
Anderson, M., et al., "A Solid-Phase Approach to the Phallotoxins: Total Synthesis of [Ala7]-Phalloidin," J. Org. Chem. (2005) 70, pp. 4578-4584.

*Primary Examiner* — Karlheinz R Skowronek
*Assistant Examiner* — Mindy Newman
(74) *Attorney, Agent, or Firm* — Jeffrey A. McKinney; McKinney Law Group APC

(57) ABSTRACT

The present invention relates to novel phalloidin derivatives and their fluorescent dye conjugates. These new compounds may be used in studies of actin dynamics in living systems. The present invention also relates to methods for preparing such compounds. The synthesis routes combine solid-phase and solution phase peptide synthesis, and has great advantage for efficient preparation of a diverse library of the phalloidin derivatives, especially for the synthesis of phalloidin.

9 Claims, 7 Drawing Sheets

H-Ala-Trp-Dap(Boc)-Ala-DThr(tBu)-Cys(Trt)-cis-Hyp-OH

Phalloidin-Dap[7]

5-TAMRA, NHS ester

PREPARATION OF PHALLOIDIN AND ITS DERIVATIVES

This application claims the benefit of priority from U.S. Provisional Patent Application Ser. No. 61/463,422, filed Feb. 17, 2011, the disclosure of which is explicitly incorporated by reference herein.

FIELD OF THE INVENTION

The present invention relates to novel phalloidin derivatives and their conjugates, which can bind strongly to F-actin, thus stabilizing the structures of the cytoskeleton. Phalloidin biotin and fluorescent conjugates provide a convenient tool for use in studies of actin dynamics in living systems. The invention also relates to the methods for phalloidin derivative synthesis, which combine the solid-phase and solution phase peptide synthesis, and have great advantage for efficient preparation of a diverse library of the phalloidin derivatives, especially for the synthesis of phalloidin.

BACKGROUND OF THE INVENTION

The chemistry and bioactivity of phallotoxins, which are one of the main groups of fungal toxins isolated from poisonous mushroom *Amanita phalloides*, have been studied systematically for over 100 years (For review, see: Wieland, T. *Peptides of Poisonous Amanita mushrooms*; Springer-Verlag: New York, 1986). The bicyclic phallotoxins are cross-linked by a thioether between the side chains of tryptophan and cysteine residues. The tryptophan residue is substituted by a sulfur group in the 2-position of the indole ring, which is named trypthionine. The phallotoxins bind strongly to filamentous actin (F-actin), not to its monomeric form, G-actin. Actin is a collective name for a class of proteins of about 43 kD, which has been detected as a type of cytoskeletal protein and isolated from many sources. The toxins accelerate the polymerization of G-actin and stabilize F-actin, thus disturbing the F-actin and G-actin equilibrium of this cytoskeletal protein. The bioactivity of the toxins depends on the molecular shape that is critical for toxins' binding to the target proteins. Any change of the molecular conformation, such as removing the sulfur-containing bridges or splitting the peptide bonds, results in the loss of toxicity.

Phallotoxins, such as phalloidin, phallacidin and phalloin are bicyclic heptapeptides that differ by the amino acid residues in the peptides. The structure of the selected phallotoxins is shown in Formula 1.

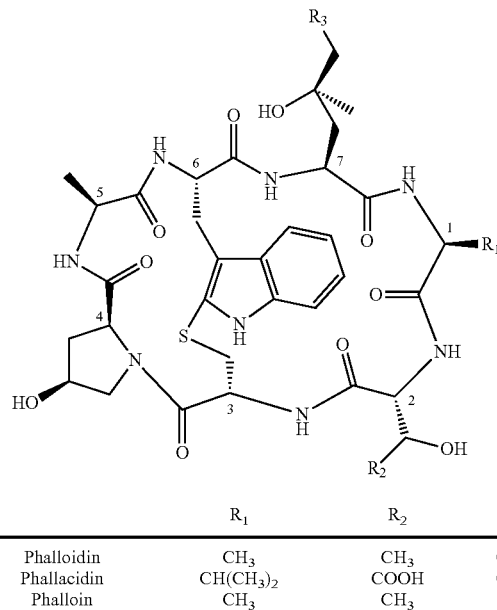

Formula 1. The general formula of the phallotoxins

| | $R_1$ | $R_2$ | $R_3$ |
|---|---|---|---|
| Phalloidin | $CH_3$ | $CH_3$ | OH |
| Phallacidin | $CH(CH_3)_2$ | COOH | OH |
| Phalloin | $CH_3$ | $CH_3$ | H |

All three peptides contain a thioether bridge linking L-Cysteine ($Cys^3$) and L-Tryptophan ($Trp^6$), a cis epimer of 4-hydroxy-L-Proline (cis-$Hyp^4$), and an L-Alanine ($Ala^5$). At position 1 and 2, both phalloidin and phalloin have an L-Alanine ($Ala^1$) and a D-Threonine ($DThr^2$), while phallacidin has an L-Valine ($Val^1$) and a β-hydroxy-D-Asparatic acid ($DAsp^2$). At position 7, both of phalloidin and phallacidin contain an unusual γ,δ-dihydroxy-L-Leucine (γ,δ-di-OH-$Leu^7$), while phalloin has a γ-hydroxy-L-Leucine (γ-OH-$Leu^7$).

The fluorescent phallotoxins used as probes for actin were introduced in 1979 (Wulf, E.; Deboben, A.; Bautz, F. A.; Faulstich, H.; Wieland, T. *Proc. Natl. Acad. Sci. USA* 1979, 76, 4498-4502) after the first fluorescent phallotoxin was synthesized from the reaction of fluorescein-isothiocyanate with amino-functionalized derivative of ketophalloidin (Wieland, T.; Deboben, A.; Faulstich, H. *Liebigs Ann. Chem.* 1980, 416-424). Since then the fluorescent phallotoxins have been widely applied in biological research, especially in histological applications. For example, the fluorescent phallotoxins have been used for the visualization of F-actin fibers by staining a variety of cells, which provide a convenient method for labeling, identifying, and quantifying F-actin in muscle and non-muscle cells from different species of plants and animals. (More examples, see: Faulstich, H,; Zobeley, S.; Rinnerthaler, G.; Small, J. V. *J. Muscle Res. Cell Motility*, 1988, 9, 370-383.; Szczesna, D.; Lehrer, S. S. *J. Muscle Res. Cell Motility*, 1993, 14, 594-597.; Prochniewicz-Nakayama, E,; Yanagida, T.; Oosawa, F. *J. Cell Bio.* 1983, 97, 1663-1667.; Small, J.; Zobeley, S.; Rinnerthaler, G.; Faulstich, H. *J Cell Sci.*, 1988, 89, 21-24.; Ao, X.; Lehrer, S. S. *J. Cell Sci.*, 1995, 108, 3397-3403.; Wang, K.; Feramisco, J. R.; Ash, J. F. *Methods Enzymol.*, 1982, 85,514-562.; Adams, A. E. M.; Pringle, J. R. *Methods Enzymol.*, 1991, 194, 729-731.; Schmit, A. C.; Lambert, A. M. *The Plant Cell*, 1990, 2, 129-138.; Mahaffy, R. E.; Pollard, T. D. *Biochemistry*, 2008, 47, 6460-6467.; Li, K.; Pu, K. Y.; Cai, L.; Liu, B. *Chem. Mater.* 2011, 23, 2113-2119.; An, M.; Wijesinghe, D.; Andreev, O. A.; Reshetnyak,Y. K.; Engelnian, D. M. *Proc. Natl. Acad. Sci. USA* 2010, 107, 20246-20250.

Since the structures of phallotoxins have been recognized, a substantial amount of synthetic work on natural and non-natural analogues of these bicyclic peptides has been carried out, especially in Wieland's laboratory (Wieland, T. *Peptides of Poisonous Amanita mushrooms*; Springer-Verlag: New York, 1986). Based on the structure-bioactivity relationship studies of phallotoxins, the interaction of phallotoxins with the target protein, F-actin, occurs at the left side 15-membered ring of the molecule (Formula 1), which contains amino acid residues at position 3, 4, 5, 6. Side chains at positions 1 and 2 play a minor role, while the role of side chain at 7 is completely insignificant.

Some functional groups, such as the amino group, are introduced to the side chain-7 and provide a convenient route to attach the fluorophores. For example, [D-Abu$^2$-Lys$^7$]-phalloin has been made in solution-phase peptide synthesis and its rhodamine conjugate was obtained by reaction of the lysine analog with tetramethyl-rhodamine isothiocyanate (Wieland, T.; Miura, T.; Seeliger, A. *Int. J. Pept. Protein Res.* 1983, 21, 3-10). More recently, [Glu$^7$]-phalloidin was synthesized by a solid-phase peptide synthesis route. The glutamic acid is introduced to the cyclic peptide both as a handle for linkage to resins and as a reactive site for conjugating the tetramethyl-rhodamine cadaverine (Schuresko, L. A.; Lokey, R. S. *Angew. Chem. Int. Ed.*, 2007, 46, 3547-3549).

The synthesis of the phalloitoxin peptides comprises: (1) the normal coupling of amino acids for generation of the peptide chains, (2) the formation of thioether linkage between tryptophan and cysteine, and (3) the cyclization of the linear peptides by intramolecular head and tail coupling. Based on the key step, the formation of trypthionine, the following routes are used for synthesis of phalloidin derivatives.

Route 1: The thiol of the cysteine residue in one peptide fragment is converted to the corresponding sulfenyl chloride. The S-chloride then reacts with the indole of the tryptophane residue in another peptide fragment to form the trypthionine moiety. The following two cyclization reactions of the double peptide give the bicyclic peptide.

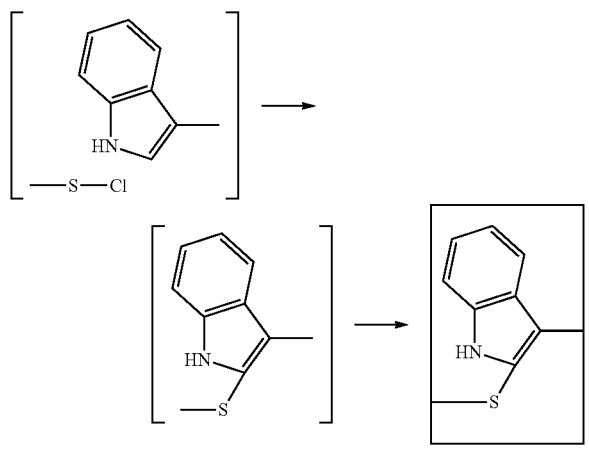

For example, see: Fahrenholz, F.; Faulstich, H.; Wieland, T. *Liebigs Ann. Chem.*, 1971, 743, 58-61; Munekata, E.; Faulstich, H.; Wieland, T. *Liebigs Ann. Chem.*, 1977, 1758-1765; Wieland, T.; Jochum, C.; Faulstich, H. *Liebigs Ann. Chem.*, 1969, 727,138-142.

Route 2: L-3a-hydroxy-1,2,3,3a,8,8a-hexahydropyrrolo[2,3-b]indole-2-carboxylic acid (Hpi), oxidation product of L-tryptophan by peroxy acid, reacts with thiols under acidic condition to yield 2-thioethers of L-tryptophan (Saviage-Fontana reaction, see: Saviage, W. E.; Fontana, A. *Int. J. Pept. Protein Res.* 1980, 15, 102-112.; *J. Chem. Soc., Chem. Comm.*, 1976, 600-601.; *Aust. J. Chem.*, 1975, 28, 2275-2278). The linear peptides containing a cysteine residue and Boc-protected Hpi are synthesized by a solution-phase peptide synthesis method. The first cyclization forms the intramolecular indolyl-thioethers under the Savige-Fontana reaction conditions, the second cyclization gives the final phalloidin derivatives by intramolecular head-tail coupling.

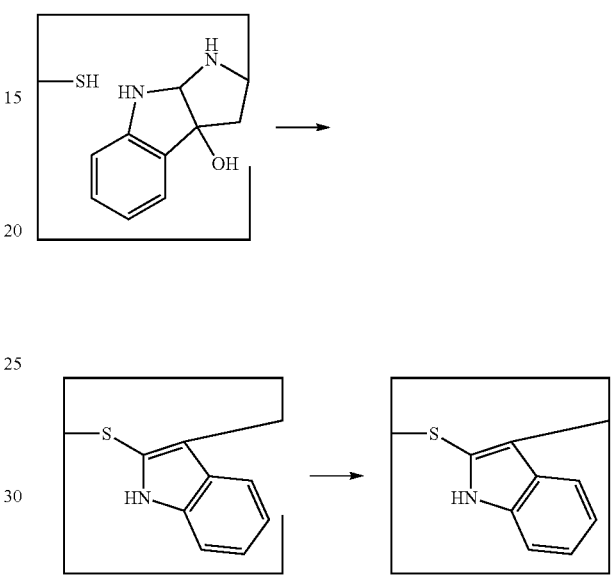

For example, see: Wieland, T.; Miura, T.; Seeliger, A. *Int. J. Pept. Protein Res.* 1983, 21, 3-10; Zanotti, G.; Falcigno, L.; Saviano, M.; D'Auria, G.; Bruno, B. M.; Campanile, T.; Paollilo, L. *Chem. Eur. J.* 2001, 7, 1479-1485; Falcigno, L.; Costantini, S.; D'Auria, G.; Bruno, B. M.; Zobeley, S.; Zanotti, G. Paollilo, L. *Chem. Eur. J.* 2001, 7, 4665-4673.

Route 3: The cyclic peptide containing tryptophan and S-tritylcysteine is oxidized by iodine to form tryptophan-2-thioether. The intermediate is sulfenyl iodide from the reaction of S-trityl group with iodine. Under some conditions, such as in dilute solution, the further reaction of sulfenyl iodide with S-trityl group to form dimeric disulfide is suppressed and the intramolecular reaction with the indole of tryptophan to form thioether is favored (Sieber, P.; Kamber, B.; Riniker, B.; Rittel, W. *Helv. Chim. Acta,* 1980, 63, 2358-2363). Recently, by using this strategy, Glu$^7$-phalloidin was synthesized using solid-phase synthesis (Schuresko, L. A.; Lokey, R. S. Angew. *Chem. Int. Ed.,* 2007, 46, 3547-3549.; US patent, 2011, U.S. Pat. No. 7,964,702).

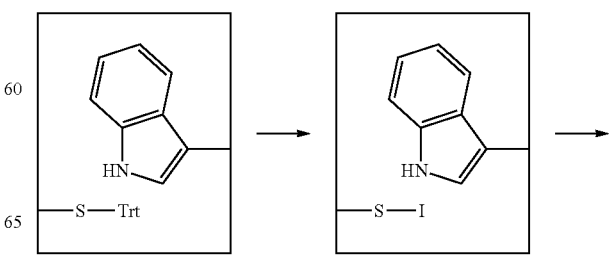

-continued

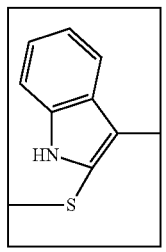

The existing synthetic routes successfully make a number of phallotoxin derivatives. However, each of these routes has drawbacks, such as low yields resulting from multi-step solution-phase peptide synthesis or time-consuming synthesis of the key intermediate. The previous synthesis of phallotoxins and their analogues mainly uses large scale solution-phase peptide synthesis techniques, especially through route 1 and route 2. A solid-phase synthetic approach to Ala[7]-phalloidin has been developed (Anderson, M.; Shelat, A. A.; Guy, R. K. J. Org. Chem., 2005, 70, 4578-4584). The key intermediates, such as protected cis-Hyp and thioether linked Trp[6]-Cys[3] unit, are still prepared in solution. This method contains two sequential resin-bound macro-cyclization reactions. The second reaction is sluggish and results in the low overall yield due to the formation of oligomers from the side reaction.

In the procedure of solid-phase synthesis of Glu[7]-phalloidin through route 3, the direct thionation of the indole of tryptophan in the solid phase produces a high yield of the final product (Schuresko, L. A.; Lokey, R. S. Angew. Chem. Int. Ed, 2007, 46, 3547-3549). However, this method is more expensive to perform for large scale synthesis because of the low resin loading that is necessary for successful on-resin cyclizations. Due to the vital importance of phallotoxin derivatives, any conceptually new and practical method for the synthesis of these compounds is of special significance. In this invention, we disclose a new method to make novel functionalized phalloidin derivatives and their fluorescent dye conjugates.

SUMMARY OF THE INVENTION

The present invention relates to novel phalloidin derivatives and their fluorescent dye conjugates. These new compounds may be used in studies of actin dynamics in living systems. The present invention also relates to methods for preparation of such compounds In one aspect the present invention provides a compound. The compound is of the following structure:

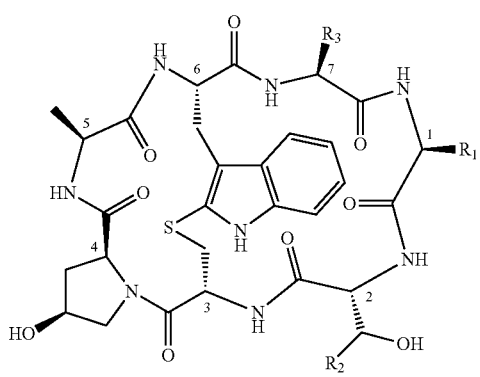

wherein $R_1$, $R_2$, $R_3$ are each independently selected from the group consisting of hydrogen, alkyl, cycloalkyl, heterocycloalkylaryl, heteroaryl, acyl, acylalkyl, carboxy, carboxamido, trialkylsilyl, aryldialkyl, hydroxy, alkoxy, aryloxy, heteroaryloxy, chloro, bromo, fluoro, iodo, thio, alkylthio, arylthio, acyclthio, amino, alkylamino, dialkylamino, acylamino, arylamino, diarylamino, carboxamido.

In another aspect, the present invention provides a method of making the compound shown above. The method involves the following steps: synthesizing a linear heptapeptide on a resin; cleaving the heptapeptide from the resin; performing head-to-tail coupling on the heptapeptide to produce a cyclic peptide; forming a thioether by direct indole thionation, thereby making the compound.

DETAILED DESCRIPTION OF THE INVENTION

Figure 1:
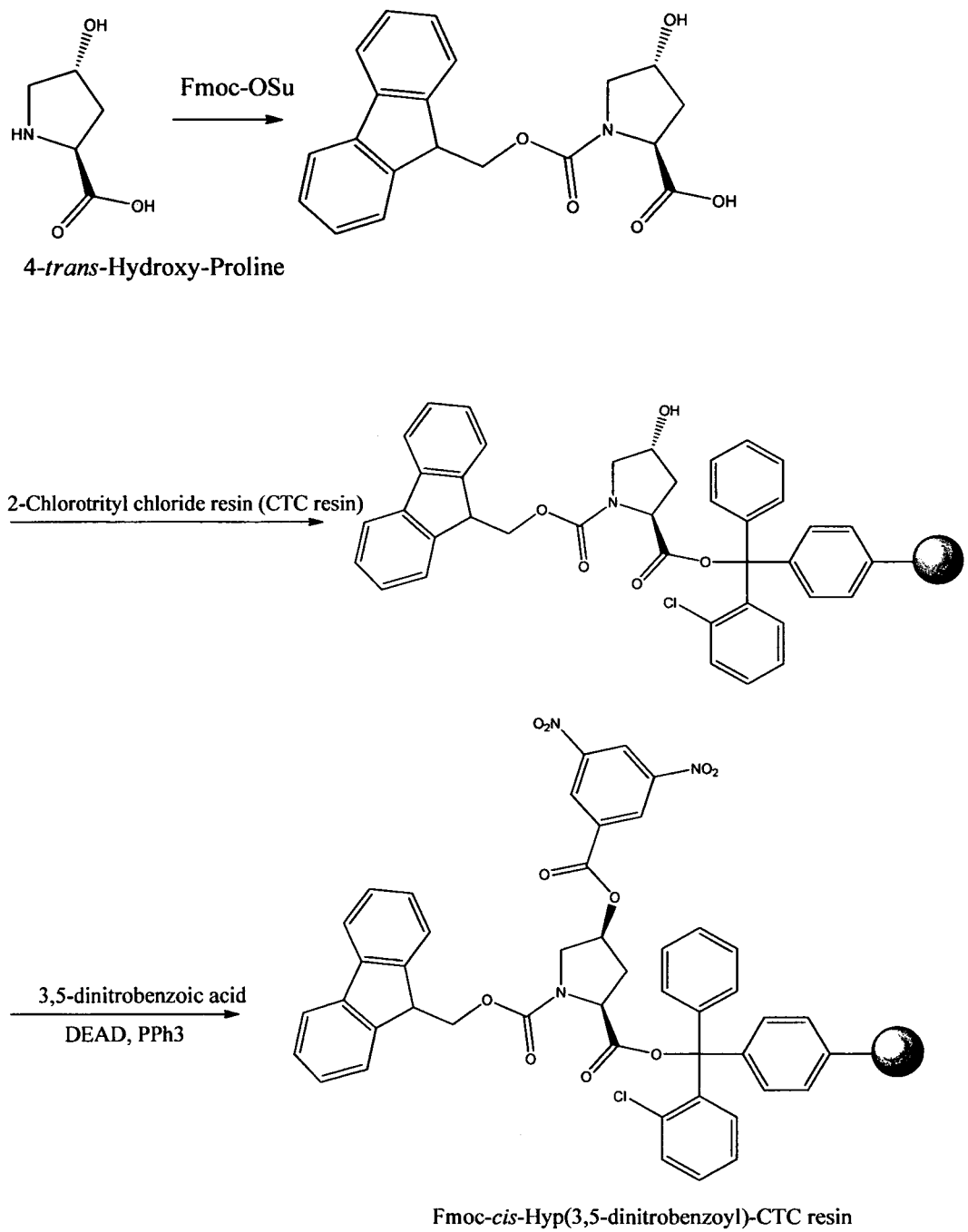
FIG. 1 shows the preparation of Fmoc-cis-Hyp(3,5-dinitrobenzoyl)-CTC resin.

The present invention relates to novel phalloidin derivatives and their conjugates, which can bind strongly to F-actin, thus stabilizing the structures of the cytoskeleton. Phalloidin biotin and fluorescent conjugates provide a convenient tool for use in studies of actin dynamics in living systems. The invention also relates to the methods for phalloidin derivative synthesis, which combine the solid-phase and solution phase peptide synthesis, and have great advantage for efficient preparation of a diverse library of the phalloidin derivatives, especially for the synthesis of phalloidin.

The compounds of the present invention are represented by the following Formula A:

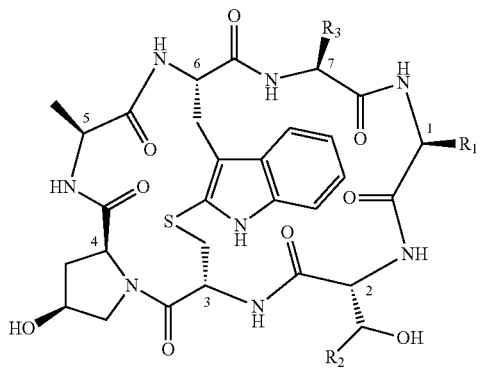

Formula A wherein $R_1$, $R_2$, $R_3$ are each independently selected from the group consisting of hydrogen, alkyl (e.g., $CH_3$, $CH_2CH_3$, $CH_2CH_2CH_3$, $CH(CH_3)_2$), cycloalkyl (e.g., cyclopropyl, cyclobutyl, cyclopentyl, cyclohexyl), heterocycloalkyl, aryl, heteroaryl (e.g., furanyl, indolyl, thiophenyl), acyl, acylalkyl, carboxy, carboxamido, trialkylsilyl, aryldialkyl, hydroxy, alkoxy, aryloxy, heteroaryloxy, chloro, bromo, fluoro, iodo, thio, alkylthio, arylthio, acyclthio, amino, alkylamino, dialkylamino, acylamino, arylamino, diarylamino, carboxamido.

In one embodiment of the invention, the phalloidin derivatives of the invention are of the Formula A-1.

In one embodiment of the invention, the phalloidin derivatives of the invention are of the Formula A-2

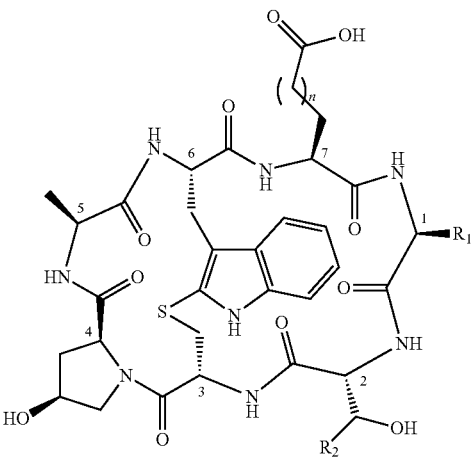

Formula A-2

$R_1$ and $R_2$ of Formula A-2 are independently alkyl groups (e.g., $CH_3$), with one embodiment being where $R_1$ and $R_2$ are both $CH_3$. The symbol "n" represents an integer selected from the integers 0, 1, 2, 3 or 4.

In one embodiment of the invention, the phalloidin derivatives of the invention are of the Formula A-3

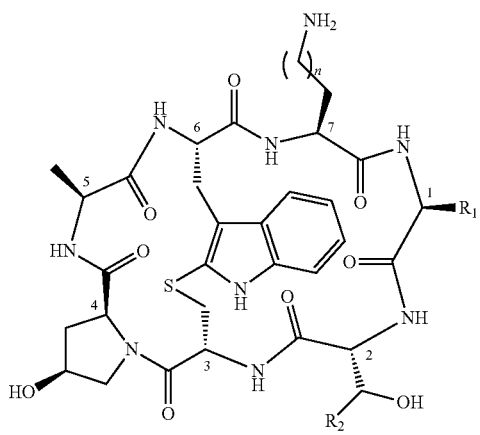

Formula A-1

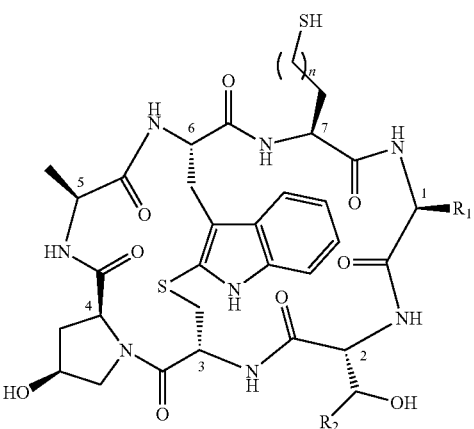

Formula A-3

$R_1$ and $R_2$ of Formula A-1 are independently alkyl groups (e.g., $CH_3$), with one embodiment being where $R_1$ and $R_2$ are both $CH_3$. The symbol "n" represents an integer selected from the integers 0, 1, 2, 3 or 4.

$R_1$ and $R_2$ of Formula A-3 are independently alkyl groups (e.g., $CH_3$), with one embodiment being where $R_1$ and $R_2$ are both $CH_3$. The symbol "n" represents an integer selected from the integers 0, 1, 2, 3 or 4.

In one embodiment of the invention, the phalloidin derivatives of the invention are of the Formula A-4

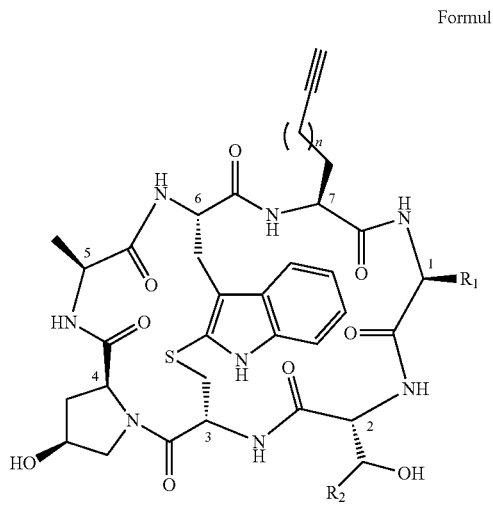

Formula A-4

$R_1$ and $R_2$ of Formula A-4 are independently alkyl groups (e.g., $CH_3$), with one embodiment being where $R_1$ and $R_2$ are both $CH_3$. The symbol "n" represents an integer selected from the integers 0, 1, 2, 3 or 4.

The choice of functional groups being introduced into the phalloidin at position 7 depends on the reactive group of the dyes that are conjugated to the toxins. The fluorescent dyes usually contain a reactive group, such as, an activated ester of a carboxylic acid (typically a succinimidyl ester of a carboxylic acid), an isocynate or isothiocynate, a reactive amine, an acyl azide, an acyl nitrile, an aldehyde, an alkyl halide, an anhydride, an aniline, an aryl halide, an azide, an aziridine, a boronate, a haloacetamide, a hydrazine, a hydrazide, a maleimide.

When an amino group (—$NH_2$) is introduced, the phalloidin derivatives (Formula A-1) are particularly useful for conjugation with dyes containing an amine-active group, such as, activated ester of carboxylic acid (typically a succinimidyl ester of carboxylic acid), an isocynate or isothiocynate.

When a hydroxycarbonyl group (—COOH) is introduced, the phalloidin derivatives (Formula A-2) are particularly useful for conjugation with dyes containing reactive amine, including a cadaverine or ethylenediamine.

When a hydrosulfuryl group (—SH) is introduced, the phalloidin derivatives (Formula A-3) are particularly useful for conjugation with dyes containing thiol-active group, such as haloacetamide, maleimide.

When a terminal alkyne is introduced, the phalloidin derivatives (Formula A-4) are particularly useful for conjugation with dyes containing azide via click chemistry.

The invention disclosed here provides methods for synthesizing phalloidin derivatives, which combine solid-phase and solution phase peptide synthesis. The methods have great advantage for efficient preparation of a diverse library of the phalloidin derivatives, especially for the synthesis of phalloidin. A feature of this invention is the efficient preparation of linear heptapeptides, the precursor of the phalloidins, through a solid-phase approach. Another feature of the invention is post-cleavage cyclization of the heptapeptide and subsequent direct thionation of indole of tryptophan by iodine oxidation in solution to form bicyclic peptides in good yields.

A general description for the synthesis of phalloidin and its derivatives in the present invention is described as follows: a linear heptapeptide is synthesized using solid phase peptide synthesis technology on an appropriate resin (e.g., chloro trityl chloride resin) and protecting group chemistry (e.g., Fmoc chemistry); one or more protecting groups are removed from the resin-bound heptapeptide; the heptapeptide is cleaved from the resin; head-to-tail coupling of the heptapeptide is effected to provide a cyclic peptide; thioether formation is achieved by direct indole thionation; removal of any remaining protecting groups results in the synthesis of phalloidin or its derivatives.

A more specific description of the synthesis of phalloidin and its derivatives in the present invention is described as follows:

A linear heptapeptide is synthesized by solid phase peptide synthesis technology on 2-chloro trityl chloride resin (CTC) using Fmoc chemistry.

Fmoc-trans-4-hydroxy-proline is loaded to 2-chloro trityl chloride resin via the C-terminal attachment. By using 3,5-dinitrobenzoic acid, the configuration of 4-hydroxy-proline is inverted under the Mitsunobu reaction condition on-resin. After the reaction is complete, the resulting Fmoc-cis-Hyp(3,5-dinitrobenzoyl)-CTC resin is easily obtained by washing off the excess reagents. The 3,5-dinitrobenzoyl side chain protecting group remains until the completion of linear heptapeptide synthesis on resin (see FIG. 1).

Fmoc-cis-Hyp(3,5-dinitrobenzoyl)-CTC resin is treated with 20% piperidine in DMF to remove Fmoc and the resulting H-cis-Hyp(3,5-dinitrobenzoyl)-CTC resin is coupled with selected amino acids to assemble the desired linear heptapeptides by using standard Fmoc chemistry. The coupling reagents are HBTU/HOBt/NMM/DMF or DIC/HOBt/DMF. Progress of each coupling is generally confirmed by standard Kaiser and chloranil tests, as well as microscale cleavage followed by HPLC and mass spectral analysis.

After the couplings are complete, the Fmoc in N-terminal and side chain protecting group 3,5-dinitrobenzoyl on hydroxyproline are removed by 2% hydrazine in DMF when the peptide is still on resin. Then the linear peptide is cleaved from resin using the cocktail mixture consisting of TFE/HOAc/DCM (2/2/6). Next, head to tail coupling reaction of the linear peptide is carried out in dilute DMF solution with PyBOP/DIEA to afford cyclic peptide in high yield.

The formation of thioether, the key step of phalloidin synthesis, is achieved by direct thionation of indole of tryptophan by iodine oxidation. Final removal of other protecting group by suitable cocktail mixture affords the crude bicyclic peptide. RP-HPLC purification of the crude gives the desired phalloidin derivative over 95% purity in reasonable yield.

Figure 2:
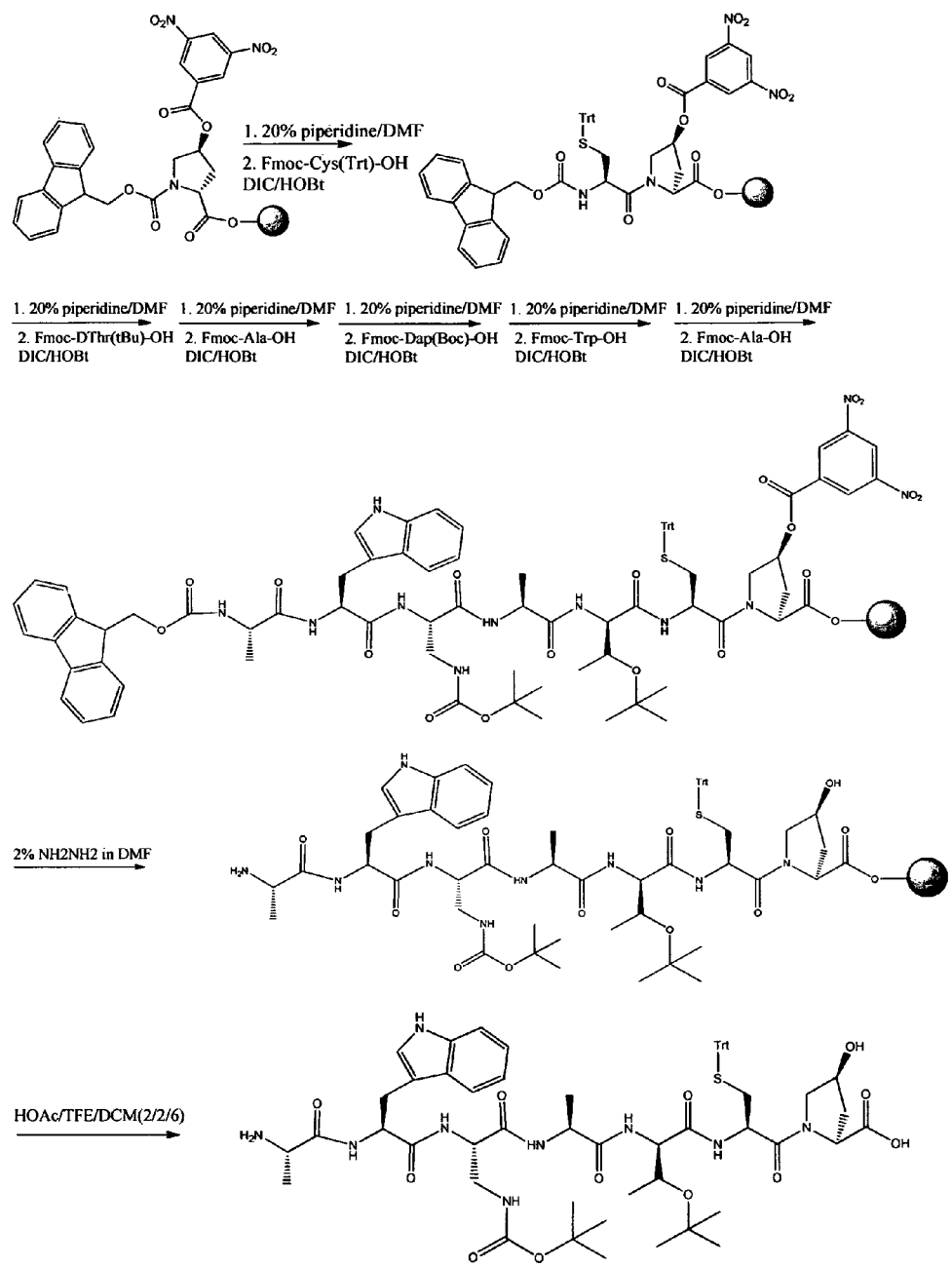
FIG. 2 shows the solid phase synthesis of linear heptapeptide (H-Ala-Trp-Dap(Boc)-Ala-DThr(tBu)-Cys(Trt)-cis-Hyp-OH).
Figure 3:
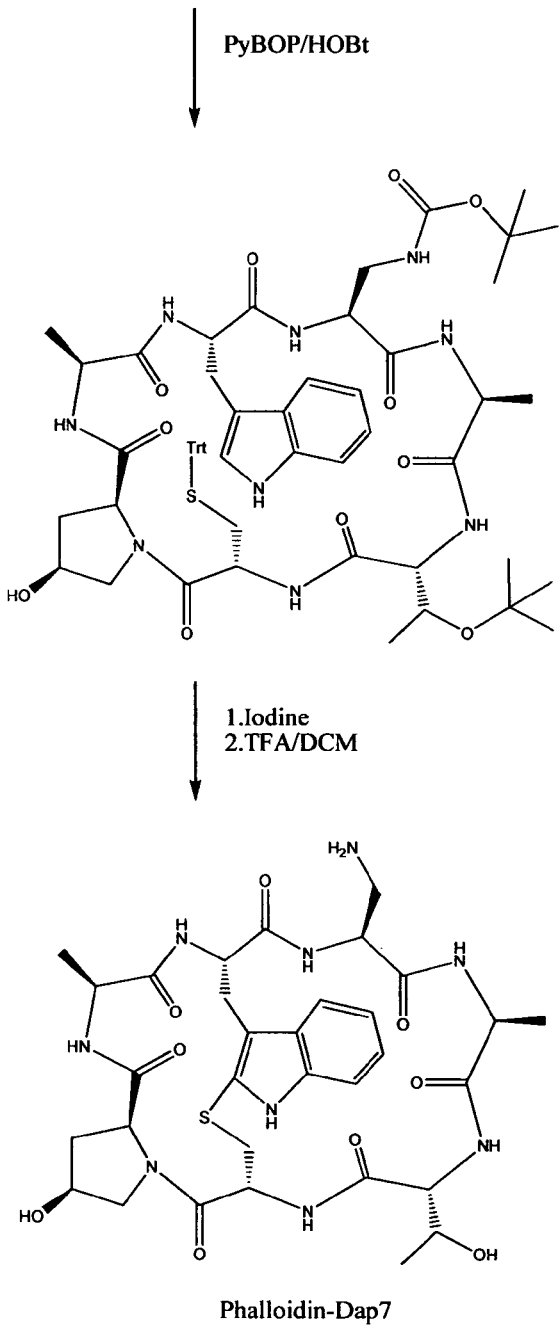
FIG. 3 shows the synthesis of Phalloidin derivative: Phalloidin-Dap[7].
Figure 4:
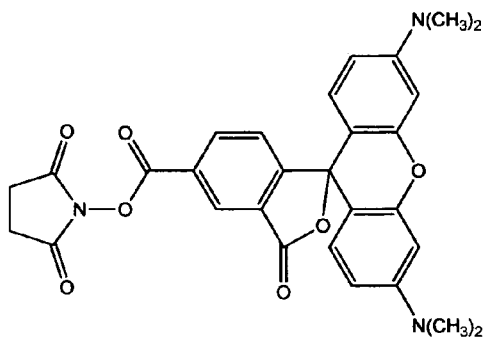
FIG. 4 shows the conjugation of a fluorescent dye to Phalloidin-Dap[7].
Figure 4:
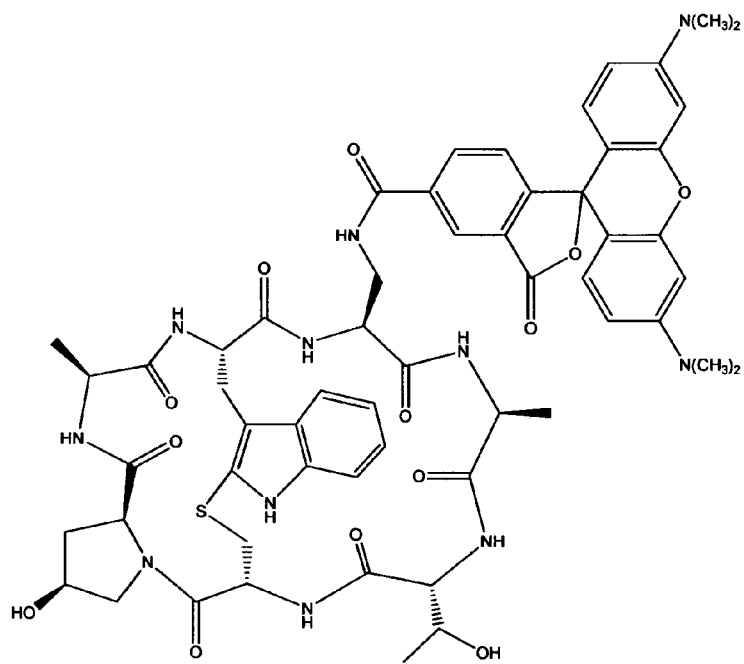

Based on the functional groups introduced to the peptide, the corresponding fluorescent dye is conjugated to the peptide to afford the fluorescent phalloidin derivative (see FIGS. 2, 3 and 4).

An even more specific description of the synthesis of phalloidin and its derivatives in the present invention is described as follows:

1. Loading N-Fmoc-trans-4-hydroxy-proline on 2-chlorotrityl chloride resin to give Fmoc-transHyp-CTC resin.
2. Inverting configuration on the resin by using 3,5-dinitrobenzoic acid under the Mitsunobu condition to afford Fmoc-cisHyp(3,5-dinitrobenzoyl)-CTC resin.
3. Using the product of step 2 as starting material, in a standard Fmoc peptide synthesis method, to couple various selected amino acids residues to get linear peptides on resin, taking peptide A (Formula A, n=0) as an example, Fmoc-Ala-Trp-Dap(Boc)-Ala-DThr(tBu)-Cys(Trt)-cisHyp(3,5-dinitrobenzoyl)-CTC resin.
4. Treating the product of step 3 with a solution of hydrazine in DMF to remove the N-terminal Fmoc group and side chain protection group (3,5-dinitrobenzoyl) of cis-Hyp, same example as above: H-Ala-Trp-Dap(Boc)-Ala-DThr(tBu)-Cys(Trt)-cisHyp-CTC resin.
5. Cleaving the product of step 4 with a solution comprising trifluoroethanol/acetic acid/dichloromethane to get a partially protected linear peptide, same example as above: H-Ala-Trp-Dap(Boc)-Ala-DThr(tBu)-Cys(Trt)-cisHyp-OH.
6. Cyclizing of the product of step 5 to get a cyclic peptide, same example as above: c[Ala-Trp-Dap(Boc)-Ala-DThr(tBu)-Cys(Trt)-cisHyp].
7. Oxidizing the product of step 6 with iodine to form a thioether between cysteine and tryptophan, same example as above:

c[Ala-Trp-Dap(Boc)-Ala-DThr(tBu)-Cys-cisHyp]
|_____|

8. Treating the product of step 7 with a solution of TFA/DCM (1:1) to remove the side chain protection to get crude peptide if necessary, same example as above: Palloidin-[Dap$^7$], c[Ala-Trp-Dap-Ala-DThr-Cys-cisHyp]
|_____|

9. Purifying the crude peptide of step 8 by reverse-phase HPLC to get peptide with purity over 95%.
10. Conjugating selected fluorescent dyes with the peptide of step 9 to give final fluorescent phalloidin derivatives, same example as above:

c[Ala-Trp-Dap(5-TAMRA)-Ala-DThr-Cys-cisHyp]
|_____|

EXAMPLES

The examples described below are in connection with preferred or illustrative embodiments of the present invention, and also are given to illustrate the practice of this invention. These embodiments are not intended to be exhaustive or limiting of the invention. Rather, the invention is intended to cover all alternatives, modifications and equivalents included within its spirit and scope, as defined by the appended claims.

Example 1

Preparation of Fmoc-trans-Hyp-OH:
To a suspension of H-trans-Hyp-OH (122.5 g, 362 mmol) in THF/H$_2$O (100 mL/200 mL) is added 2N Na$_2$CO$_3$ (250 mL), along with addition of a suspension of Fmoc-OSu in THF (700 mL). The mixture is stirred at room temperature overnight. The mixture is diluted with H$_2$O (2700 mL) and extracted with ether/petroleum ether (500 mL/500 mL) The aqueous layer is acidified by 6N HCl and then extracted with ethyl acetate (1×1000 mL, 1×500 mL). The combined extract is washed with brine once and dried over Na$_2$SO$_4$. After removal of most of solvent, the residue is treated with ethyl ether (200 mL). The white solid is filtered and dried under vacuum. Yield: 125.8 g (356 mmol, 98%)

Example 2

Attachment of Fmoc-trans-Hyp-OH to 2-chlorotrityl chloride resin (CTC resin):
To the suspension of 2-Chlorotrityl chloride resin (100 g, 1.4 mmol/g) in DMF (500 mL) is added DIPEA (87.5 mL, 500 mmol), followed by a solution of Fmoc-trans-Hyp-OH (49.5 g, 120 mmol) in DMF (250 mL). The mixture is stirred at room temperature overnight. Methanol (100 mL) is added and the stirring continues for 30 min. The resin is filtered and washed with DMF (3×500 mL), DCM (3×500 mL), ether (1×500 mL). The resin is dried under high vacuum overnight. Yield of Fmoc-trans-Hyp-CTC resin: 129 g (substitution 0.58 mmol/g)

Example 3

Configuration inversion of 4-hydroxy-proline on resin: preparation of Fmoc-cis-Hyp(3,5-dinitrobenzoyl)-CTC resin:
Fmoc-trans-Hyp-CTC resin (125 g, 72.5 mmol) is swelled in anhydrous THF (1000 mL) for 20 min, and then cooled in 0° C. (ice-water bath). 3,5-Dinitrobenzoic acid (46.1 g, 217.5 mmol) and PPh$_3$ (57.0 g, 217.5 mmol) are added, followed by addition of diethyl azodicarboxylate (40% wt. in toluene, 99.1 mL, 217.5 mmol). The mixture is stirred at 0° C. for 3 h and then at room temperature overnight. After the reaction is complete (monitored by microscale cleavage and HPLC analysis), the resin is filtered and washed with DCM (3×500 mL), DMF (3×500 mL), DCM (3×500 mL), ether (1×500 mL). The resin is dried under high vacuum. Yield of Fmoc-cis-Hyp(3,5-dinitrobenzoyl)-CTC resin: 146 g (0.50 mmol/g)

Example 4

Synthesis of Phalloidin-Dap$^7$ (Dap: 2,3-diaminopropionic acid)

c[Ala-Trp-Dap-Ala-DThr-Cys-cisHyp]
|_____| a. In a manual peptide synthesis reaction vessel, Fmoc-cis-Hyp(3,5-dinitrobenzoyl)-CTC resin (2.2 g, 1.1 mmol) is swelled in DCM (30 mL) for 30 min, then filtered and washed with DMF (2×30 mL).
b. The above resin is treated with a solution of 20% piperidine in DMF twice (2×15 mL) for deprotection (Fmoc removal). After being washed with DMF (5×20 mL), H-cis-Hyp(3,5-dinitrobenzoyl)-CTC resin is obtained.
c. To a solution of Fmoc-Cys(Trt)-OH (1.93 g, 3.3 mmol) and HOBt (0.45 g, 3.3 mmol) in DMF (20 mL) is added DIC (0.51 mL, 3.3 mmol). The mixture is shaken for 20 min and added to above resin. Nitrogen is bubbled gently through the mixture for 2 hours. After the coupling is complete (monitored by Kaiser test or by microscale cleavage and subsequent HPLC, mass spectral analysis), the resin is filtered and washed with DMF (3×30 mL), DCM (3×30 mL), DMF (3×30 mL). The dipeptide is synthesized, Fmoc-Cys(Trt)-cis-Hyp(3,5-dinitrobenzoyl)-CTC.

d. Repeat the steps b) and c) to elongate the peptide chain to desired linear peptide, by using side chain protected $N^\alpha$-Fmoc-amino acids in the following order: Fmoc-D-Thr(tBu)-OH, Fmoc-Ala-OH, Fmoc-Dap(Boc)-OH, Fmoc-Trp-OH, and Fmoc-Ala-OH. Fmoc-Ala-Trp-Dap(Boc)-Ala-DThr(tBu)-Cys(Trt)-cis-Hyp(3,5-dinitrobenzoyl)-CTC e. The above linear heptapeptide on resin is treated with a solution of 2% $NH_2NH_2$ in DMF twice (2×30 mL) to remove the N-terminal Fmoc group and side chain protective group on the cis-Hyp. After being washed with DMF (5×20 mL) and ether (2×20 mL), H-Ala-Trp-Dap(Boc)-Ala-DThr(tBu)-Cys(Trt)-cis-Hyp-CTC resin is obtained.

f. The above resin is treated with a solution of DCM/HOAc/TFE (trifluoroethanol) (24/8/8 mL) for 50 min. The resin is filtered and the filtrate is concentrated. The residue is treated with ethyl ether and the solid is filtered and washed with ether and dried under vacuum. Yield of H-Ala-Trp-Dap(Boc)-Ala-DThr(tBu)-Cys(Trt)-cis-Hyp-OH: 1.3 g (1.1 mmol, 100%), MS (M+Na) Calcd. for $C_{60}H_{76}N_9O_{12}SNa$ 1170.4. found 1170.9.

g. To the solution of the above linear peptide 1.3 g (1.1 mmol) in DMF (1000 mL) is added DIPEA (1 mL, 5.5 mmol), followed by PyBOP (0.9 g, 1.7 mmol). The mixture is stirred at room temperature for 1 h. After the reaction is complete (monitored by HPLC), the mixture is concentrated. The residue is dissolved in EtOAc and the solution is washed with 5% $H_3PO_4$ (2×), brine (1×), sat'd $NaHCO_3$ (2×), brine (1×), and then dried over $Na_2SO_4$. After removal of the solvent, residue is dried under vacuum to quantitatively give crude cyclic peptide, c[Ala-Trp-Dap(Boc)-Ala-DThr(tBu)-Cys(Trt)-cis-Hyp]. MS (M+Na) Calcd. for $C_{60}H_{74}N_9O_{11}SNa$ 1152.3. found 1152.5.

h. The above crude monocyclic peptide (1.1 mmol) is dissolved in DMF (1000 mL) and 0.2 M solution of iodine in DCM (100 mL) is added. The mixture is stirred at room temperature and the reaction is monitored by HPLC until the starting material disappears. The reaction is quenched by a 0.2 M sodium citrate solution containing L-ascorbic acid. The solvent is removed and the residue is re-dissolved in $EtOAc/H_2O$. The organic layer containing peptide is collected and the aqueous layer is extracted with EtOAc three times. The combined extract is dried over $Na_2SO_4$. After removal of solvent, residue is dissolved in TFA/DCM (15 mL/15 mL) and the solution is stirred for 1 h. The solvent is removed and the peptide is precipitated by the addition of cold ethyl ether. The solid is filtered, washed with ether, dried under high vacuum. Yield of crude bicyclic peptide 0.8 g:

i. The crude peptide is purified on a preparative RP-HPLC system (C-18 column) by using a gradient of 15 to 45% B over 60 min (A: 0.1% TFA in water and B: 0.1% TFA/acetonitrile) at a flow rate of 100 mL/min. After lyophilizing, pure peptide is obtained as a white powder, 126 mg (0.173 mmol), HPLC purity over 97%. Further product characterization is carried out by mass spectrometry: M+H Calcd. for $C_{32}H_{44}N_9O_9S$ 730.8. found 730.4; and UV-Vis spectrometry: $\lambda_{max}$ 290 nm for absorption of indole of the tryptophan-2-thioether. The overall yield of the pure phalloidin-Dap[7] is 16% based on the initial resin loading.

Example 5

Conjugation of TAMRA to phalloidin-Dap[7]:

To a solution of phalloidin-Dap[7] (3 mg, 4.1 µmol) in DMF (100 µL) is added DIPEA (2 µL), followed by addition of tetramethylrhodamine-5-carboxylic acid, succinimidyl ester (5-TAMRA, NHS ester, 2 mg, 4.1 µmol) in DMF (200 µL). More DIPEA (4 µL) and DMF (100 µL) is added. The mixture is stirred at room temperature for 5 h. After the reaction is complete, the mixture is diluted with cold ethyl ether. The precipitate product is collected and further purified on preparative RP-HPLC system (0.5 inch C-4 column) by using a gradient of 0 to 55% B over 40 minutes (A: 0.1% TFA in water and B: 0.1% TFA/acetonitrile) at a flow rate of 4 mL/minute. After lyophilization, pure peptide is obtained as red powder, 3 mg, HPLC purity over 98%.

Further product characterization is carried out by mass spectrometry: M Calcd. for $C_{57}H_{63}N_{11}O_{13}S$ 1142.2. found 1142.7

Example 6

Synthesis of Phalloidin-Lys[7]

Following the procedure in example 4 from step a) to d), Fmoc-Ala-Trp-Lys(Boc)-Ala-DThr(tBu)-Cys(Trt)-cis-Hyp(3,5-dinitrobenzoyl)-CTC, is synthesized by using 1 mmol Fmoc-cis-Hyp(3,5-dinitrobenzoyl)-CTC resin as starting material and Fmoc-Lys(Boc)-OH as building block, instead of Fmoc-Dap(Boc)-OH.

Following the procedure in example 4 from step e) to i), phalloidin-Lys[7] is obtained 124 mg (0.161 mmol), with yield 16%, HPLC purity >95%, MS (M+H) Calcd. for $C_{35}H_{50}N_9O_9S$ 772.9. found 772.8.

Example 7

Synthesis of Phalloidin-Orn[7]

Following the procedure in example 4 from step a) to d), Fmoc-Ala-Trp-Orn(Boc)-Ala-DThr(tBu)-Cys(Trt)-cis-Hyp(3,5-dinitrobenzoyl)-CTC, is synthesized by using 1 mmol Fmoc-cis-Hyp(3,5-dinitrobenzoyl)-CTC resin as starting material and Fmoc-Orn(Boc)-OH as building block, instead of Fmoc-Dap(Boc)-OH.

Following the procedure in example 4 from step e) to i), phalloidin-Orn[7] is obtained 76 mg (0.10 mmol), with yield 10%, HPLC purity >95%, MS (M+H) Calcd. for $C_{34}H_{48}N_9O_9S$ 758.9. found 758.7.

Example 8

Synthesis of Phalloidin-Asp[7]

c[Ala-Trp-Asp-Ala-DThr-Cys-cisHyp]

Following the procedure in example 4 from step a) to d), Fmoc-Ala-Trp-Asp(Boc)-Ala-DThr(tBu)-Cys(Trt)-cis-Hyp(3,5-dinitrobenzoyl)-CTC, is synthesized by using 1 mmol Fmoc-cis-Hyp(3,5-dinitrobenzoyl)-CTC resin as starting material and Fmoc-Asp(OtBu)-OH as building block, instead of Fmoc-Dap(Boc)-OH.

Following the procedure in example 4 from step e) to i), phalloidin-Asp[7] is obtained 91 mg (0.120 mmol), with yield 12%, HPLC purity >95%, MS (M+H) Calcd. for $C_{33}H_{43}N_8O_{11}S$ 759.8. found 759.5.

Example 9

The synthesis of Phalloidin

c[Ala-Trp-Leu(4,5-di-OH)-Ala-DThr-Cys-cisHyp]

1. Synthesis of dipeptide containing (2S,4R)-4,5-dihydroxyleucine

Figure 5:
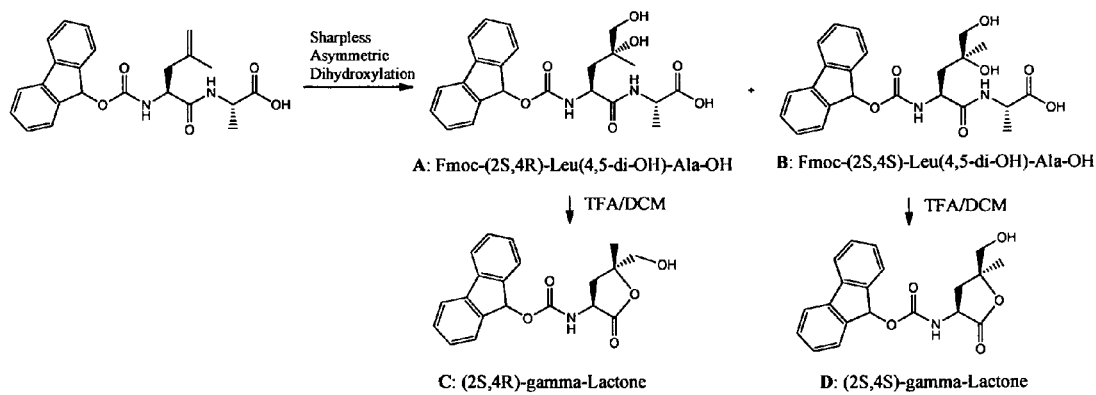
FIG. 5 shows the synthesis of dipeptide containing 4,5-dihydroxy-L-Leucine. The reaction conditions listed below provide the following, corresponding compound ratios (based on HPLC): AD-mix α (0° C.), AC (3) and BD (1); AD-mix α (room temperature), AC (2) and BD (1); AD-mix β (0° C.), AC (1) and BD (9); AD-mix β (room temperature), AC (1) and BD (7); AD mix without ligand (room temperature), AB (1) and BD (2).

Dihydroxylation of Fmoc-Leu(4,5-dehydro)-Ala-OH with AD-mix α or AD-mix β gives a mixture of diasteromers of Fmoc-Leu(4,5-di-OH)-Ala-OH with 4R or 4S configuration. The ratio of the two diasteromers cannot be determined by HPLC analysis directly. However, a sample of above products has been converted to corresponding γ-lactones by treatment with TFA in DCM and the ratios of the γ-lactone diasteromers can be determined by HPLC analysis. The results show that dihydroxylation with both AD-mix α and AD-mix β cannot give the dipeptide with a steroisomerically pure 4,5-dihydroxyleucine. However, each AD-mix dihydroxylation favors one of the two diasteromers respectively and both dipeptides are synthetic useful (FIG. 5). In a typical procedure, a solution of AD-mix a (140 g) in tent-butanol (500 mL) and water (500 mL) is cooled to 0° C. in an ice-water bath. Fmoc-Leu(4,5-dehydro)-Ala-OH (42.2 g, 100 mmol) is added and the mixture is stirred at 0° C. until the reaction is complete (overnight). The reaction mixture is quenched with sodium sulfite (150 g) and stirred for 1 h. The mixture is diluted with water (1500 mL) and extracted with ethyl acetate (2×1000 ml). The aqueous layer is collected and acidified with 6N HCl to pH 3-4 and extracted with ethyl acetate (2×1000 mL). The combined extract is washed with brine once and dried over $Na_2SO_4$. After removal of solvent, the residue is dried under vacuum. Fmoc-Leu(4,5-di-OH)-Ala-OH is obtained quantitatively.

Figure 6:
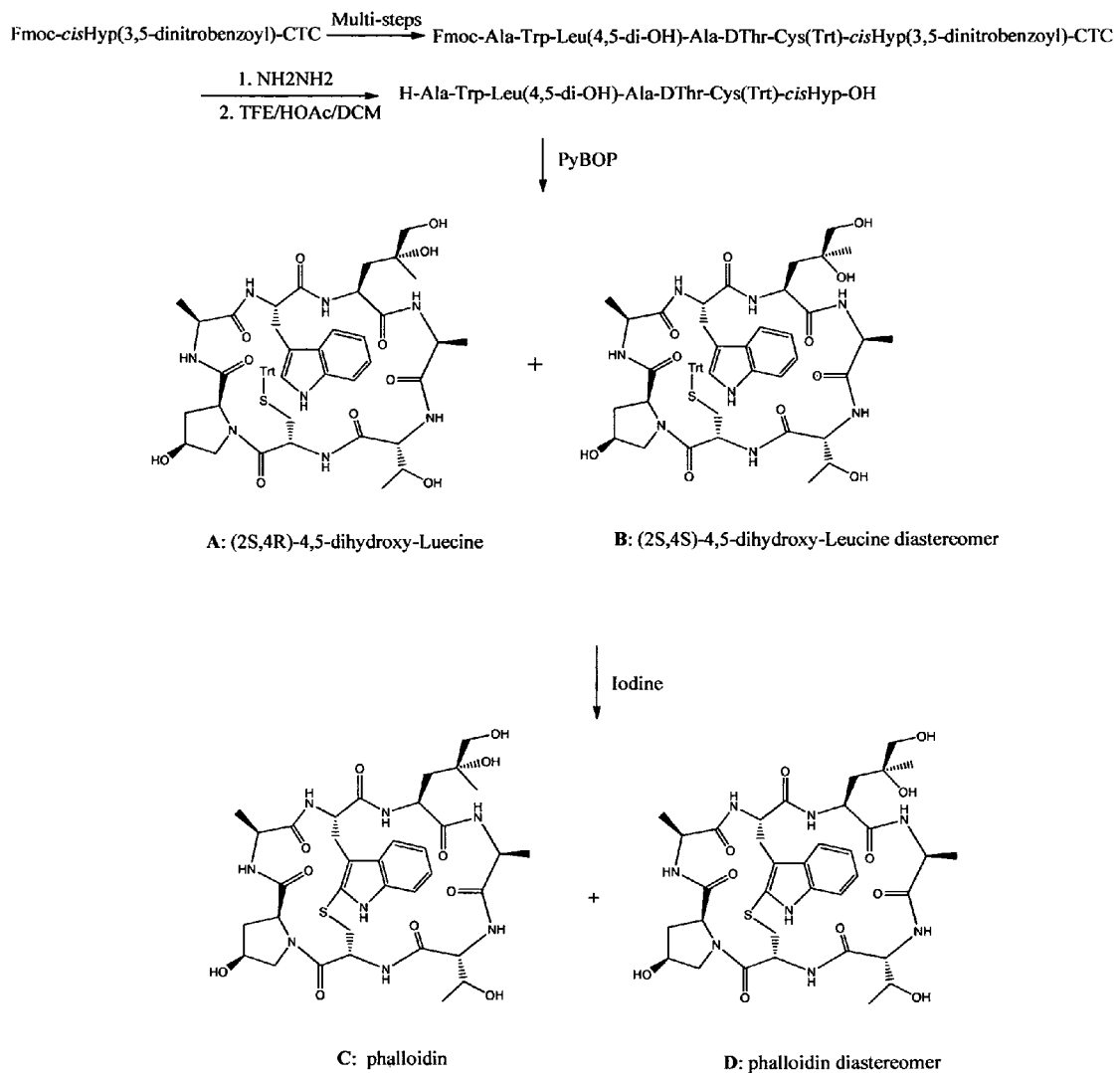
FIG. 6 shows the synthesis of phalloidin.
Figure 7:
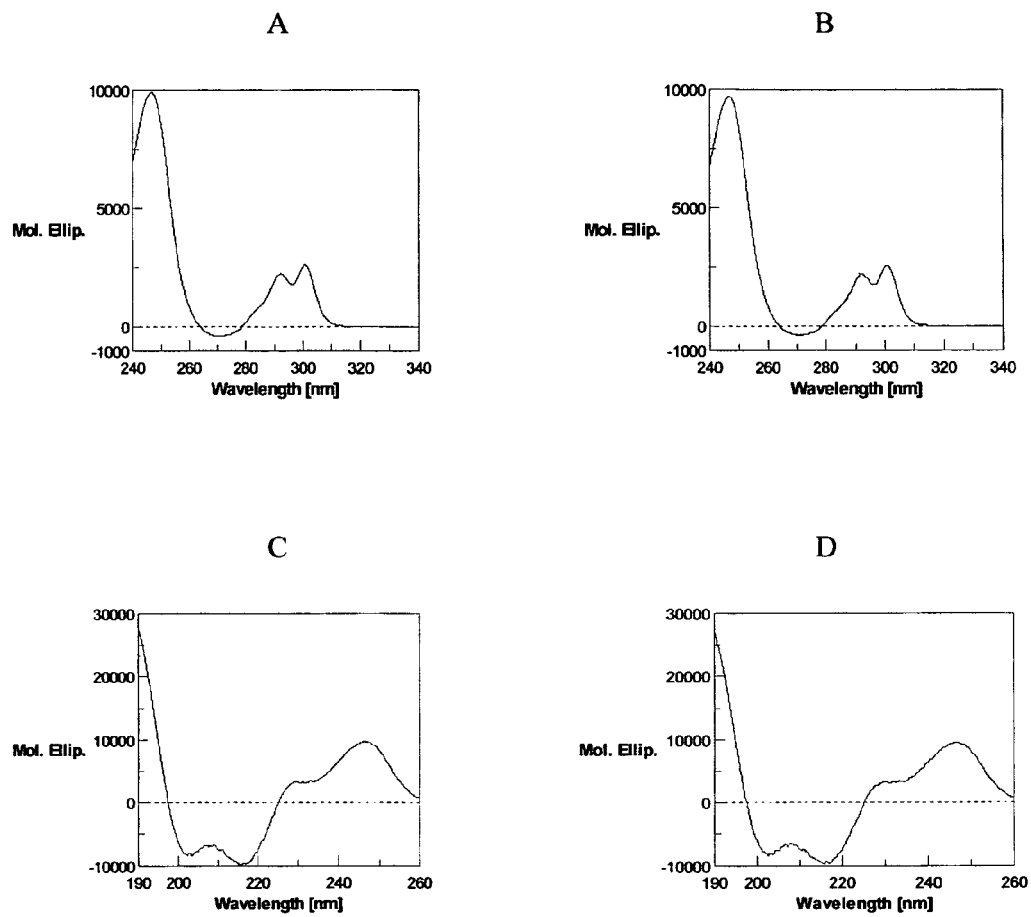
FIG. 7 shows the Circular Dichroism spectra of synthetic Phalloidin and natural Phalloidin: A is near UV CD spectra of Palloidin-Sigma (natural) (lot: 060M0867V) in water (0.5 mg/mL); B is near UV CD spectra of Palloidin (synthetic) (lot: 140-35) in water (0.5 mg/mL); C is far UV CD spectra of Phalloidin-Sigma (natural) (lot: 060M0867V) in water (0.5 mg/mL); D is far UV CD spectra of Phalloidin (synthetic) (lot: 140-35) in water (0.5 mg/mL).

2. The synthesis of Phalloidin (FIG. 6)

a. In a manual peptide synthesis vessel, Fmoc-cis-Hyp(3,5-dinitrobenzoyl)-CTC resin (20 g, 10 mmol) is swelled in DCM (200 mL) for 30 min, then filtered and washed with DMF (2×200 mL).

b. The above resin is treated with 20% piperidine in DMF (2×150 ml). After being washed with DMF (5×200 ml), H-cis-Hyp(3,5-dinitrobenzoyl)-CTC is obtained.

c. To a solution of Fmoc-Cys(Trt)-OH (17.6 g, 30 mmol) and HOBt (4.1 g, 30 mmol) in DMF (100 mL) is added DIC (4.65 mL, 30 mmol). The mixture is shaken for 20 min and added into the resin of step b. Nitrogen is bubbled gently through the mixture for 2 hours. After the coupling is complete (monitored by Kaiser test or by microscale cleavage and subsequent HPLC and mass spectral analysis), the resin is filtered and washed with DMF (3×200 mL), DCM (2×200 mL), DMF (3×200 mL). The dipeptide Fmoc-Cys(Trt)-cis-Hyp(3,5-dinitrobenzoyl)-CTC is obtained.

d. Repeat the steps b) and c) to elongate the peptide chain by using $N^\alpha$-Fmoc-amino acids or dipeptide in the following order: Fmoc-D-Thr-OH, Fmoc-Leu(4,5-di-OH)-Ala-OH, Fmoc-Trp-OH, Fmoc-Ala-OH. The linear peptide on resin is obtained, Fmoc-Ala-Trp-Leu(4,5-di-OH)-Ala-DThr-Cys(Trt)-cis-Hyp(3,5-dinitrobenzoyl)-CTC.

e. The above linear peptide on resin is treated with 2% $NH_2NH_2$ in DMF twice (2×200 mL) After being washed with DMF (5×200 mL), ethyl ether (2×100 mL), H-Ala-Trp-Leu(4,5-di-OH)-Ala-DThr-Cys(Trt)-cis-Hyp-CTC resin is obtained.

f. The above resin is treated with a solution of DCM/HOAc/TFE (240/80/80 mL) for 1 h. The resin is filtered and the filtrate is concentrated. The residue is treated with cold ethyl ether. The solid is filtered and washed with ether and dried under vacuum. Yield of H-Ala-Trp-Leu(4,5-di-OH)-Ala-DThr-Cys(Trt)-cis-Hyp-OH, 10.5 g (10 mmol, 100%). MS (M+Na) Calcd. For $C_{54}H_{65}N_8O_{12}SNa$ 1073.20. found 1074.0.

g. To a solution of above linear peptide 10.5 g (10 mmol) in DMF (8000 mL) is added DIPEA (9 mL, 50 mmol), followed by addition of PyBOP (7.8 g, 15 mmol). The mixture is stirred at room temperature. After the reaction is complete (monitored by HPLC), the mixture is concentrated by removal of solvent. The residue is dissolved in EtOAc and the solution is washed with 5% $H_3PO_4$ (2×), brine (1×), saturated $NaHCO_3$ (2×), brine (1×), and dried over $Na_2SO_4$. After removal of solvent, residue is dried under vacuum to quantitatively give crude cyclic peptide, c[Ala-Trp-Leu(4,5-di-OH)-Ala-DThr-Cys(Trt)-cis-Hyp]. MS (M+Na) Calcd. For $C_{54}H_{63}N_8O_{11}SNa$ 1055.18. found 1055.4.

h. The above crude monocyclic peptide (10 mmol) is dissolved in DMF (10 L) and 0.2 M solution of iodine in DCM (1 L) is added. The mixture is stirred at room temperature and the reaction is monitored by HPLC until the starting material disappears. The reaction is quenched by a solution of L-ascorbic acid and the pH value of the resulting solution is adjusted to 5-6 with $NaHCO_3$ solution. The solvent is removed under vacuum and the residue is re-dissolved in ethyl acetate/water (300 mL/300 mL). The organic layer is discarded and the aqueous layer containing desired bi-cyclic peptide is collected and purified on a preparative HPLC system (C-18 column) by using a gradient of 15-45% B over 60 min (A: 0.1% TFA in water and B: 0.1% TFA in acetonitrile) at a flow rate of 100 mL/min. The pure fractions are re-loaded to the system and the TFA is removed by using water/acetonitrile as elute solvent. After lyophilizing, pure peptide is obtained as a white powder, 665 mg (0.844 mmol), HPLC purity over. 95%. MS (M+Na) Calcd. For $C_{35}H_{47}N_8O_{11}SNa$ 810.85.

found 811.4. The overall yield of phalloidin is 8.4% based on the initial resin loading. By circular dichroism (CD) analysis, the synthetic phalloidin is found to be consistent with the natural phalloidin (FIG. 7).

What is claimed is:

1. A method of making the following compound:

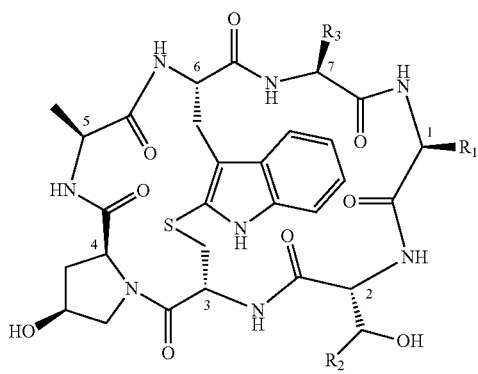

wherein $R_1$, $R_2$, $R_3$ are each independently selected from the group consisting of hydrogen, alkyl, cycloalkyl, heterocycloalkylaryl, heteroaryl, acyl, acylalkyl, carboxy, carboxamido, trialkylsilyl, aryldialkyl, hydroxy, alkoxy, aryloxy, heteroaryloxy, chloro, bromo, fluoro, iodo, thio, alkylthio, arylthio, acyclthio, amino, alkylamino, dialkylamino, acylamino, arylamino, diarylamino, carboxamido; and wherein the method comprises the following steps:
  a) synthesizing a linear heptapeptide on a resin;
  b) cleaving the linear heptapeptide from the resin;
  c) performing head-to-tail coupling on the heptapeptide to produce a cyclic peptide;
  d) forming a thioether by direct indole thionation
thereby making the compound.

2. The method according to claim 1, wherein the linear peptide is synthesized on 2-chloro trityl chloride resin using Fmoc chemistry.

3. The method according to claim 1, wherein the peptide is cleaved using a mixture of TFE, HOAc and DCM.

4. The method according to claim 1, wherein head-to-tail coupling is effected in dilute DMF solution with PyBOP/DIEA.

5. The method according to claim 1, wherein direct indole thionation is achieved by iodine oxidation.

6. The method according to claim 2, wherein synthesis of the linear peptide comprises the following steps:
  a) loading Fmoc-trans-hydroxy-proline onto 2-chloro trityl chloride resin through the C-terminal attachment; wherein the hydroxy-proline has a configuration;
  b) inverting the configuration of the hydroxy-proline under Mitsunobu reaction conditions;
  c) removing Fmoc from the inverted, resin bound hydroxyl-proline to provide an deprotected compound;
  d) coupling the deprotected compound with one or more types of amino acids to afford a resin bound heptapeptide, wherein the heptapeptide has an N-terminus;
  e) removing Fmoc from the N-terminus to provide the heptapeptide bound to the resin;
thereby synthesizing the linear heptapeptide.

7. The method according to claim 6, wherein the peptide is cleaved using a mixture of TFE, HOAc and DCM.

8. The method according to claim 7, wherein head-to-tail coupling is effected in dilute DMF solution with PyBOP/DIEA.

9. The method according to claim 8, wherein direct indole thionation is achieved by iodine oxidation.

* * * * *